United States Patent [19]
Hayafuji

[11] Patent Number: 5,634,463
[45] Date of Patent: Jun. 3, 1997

[54] NONCONTACT TYPE TONOMETER

[75] Inventor: Mineki Hayafuji, Tokyo, Japan

[73] Assignee: Kabushiki Kaisha Topcon, Tokyo, Japan

[21] Appl. No.: 358,466

[22] Filed: Dec. 19, 1994

[30] Foreign Application Priority Data

Dec. 20, 1993 [JP] Japan .................................. 5-320158

[51] Int. Cl.⁶ .......................................... A61B 3/16
[52] U.S. Cl. ............................................ 128/645; 128/652
[58] Field of Search ........................ 128/645–52

[56] References Cited

U.S. PATENT DOCUMENTS

| | | | |
|---|---|---|---|
| 4,825,873 | 5/1989 | Kohayakawa | 128/648 |
| 4,947,849 | 8/1990 | Takahashi et al. | 128/648 |
| 4,951,670 | 8/1990 | Tanaka et al. | 128/648 |
| 5,279,300 | 1/1994 | Miwa et al. | 128/648 |

FOREIGN PATENT DOCUMENTS

| | | | |
|---|---|---|---|
| 56-6772 | 2/1981 | Japan . | |
| 2223107 | 3/1990 | United Kingdom | 128/648 |

*Primary Examiner*—Angela D. Sykes
*Assistant Examiner*—John P. Lacyk
*Attorney, Agent, or Firm*—Finnegan, Henderson, Farabow, Garrett & Dunner, L.L.P.

[57] ABSTRACT

A noncontact type tonometer capable of accurately measuring intraocular pressure of a subject's eye even if the intraocular pressure is much higher than normal. The noncontact type tonometer comprises a fluid discharging device for discharging fluid toward a cornea of the eye, a corneal transfiguration detecting portion for detecting the corneal transfiguration, a pressure detecting portion for detecting discharge pressure of the fluid, and a delay circuit for determining the precise moment for stopping the operation of the fluid discharging means according to the discharge pressure detected by the pressure detecting means.

2 Claims, 4 Drawing Sheets

5,634,463

NONCONTACT TYPE TONOMETER

BACKGROUND OF THE INVENTION

1. Field of the Invention

This invention relates to an improvement of a noncontact type tonometer which is designed to measure intraocular pressure of a subject's eye by optically detecting transfiguration of the eye caused by discharging a fluid toward the eye without bringing the tonometer into contact with the eye.

2. Description of the Prior Art

This kind of noncontact type tonometer, for example, as shown in Japanese Patent Application Early Laid-open Publication No. Sho 56-6772, comprises a gas discharging device for transfiguring the eye by discharging gas toward the eye, a light source for illuminating the eye with detecting light, and a corneel transfiguration detecting means for receiving reflected light from the eye to detect the corneel transfiguration of the eye.

If the discharge pressure of the gas gradually increases, a surface of the cornea is transfigured, so that the quantity of the reflected light from the cornea temporarily increases and reaches its peak when the cornea is transfigured into an applenation state (a flat state). If the discharge pressure further increases, the surface of the cornea becomes concave and then the reflected light quantity decreases.

In a conventional noncontact type tonometer, at the time when the quantity of the reflected light from the cornea exceeds a predetermined reference level, namely before the cornea reaches an applanation state, the operation of the gas discharging device is stopped. After the operation of a piston of the gas discharging device is stopped, the discharge pressure increases for a while by inertia of the piston and then decreases. In a case where the intraocular pressure of the eye is normal, since the cornea is transfigured into the applanation state and the peak of reflected light quantity is detected when the pressure within the gas discharging device is increasing because of the inertia, the intraocular pressure can be calculated from the air pressure obtained when the peak is detected.

However, in the conventional tonometer, so to speak, with the expectation that the cornea is transfigured into the applanation state during the rise in pressure caused by the inertia of the piston, the operation of the gas discharging device is stopped. Accordingly, if the intraocular pressure of the eye is much higher than normal and an increase in quantity of the discharge pressure needed for the reflected light quantity to exceed the reference level and reach the applanation state is also larger than normal, the air pressure within the gas discharging device decreases before the cornea is transfigured into the applanation state in spite of the rise in pressure caused by the inertia. For this reason, unfavorably, the peak of the reflected light quantity cannot be detected and the measurement of the intraocular pressure cannot be carried out accurately.

SUMMARY OF THE INVENTION

It is, therefore, an object of the present invention to provide a noncontact type tonometer capable of accurately measuring the intraocular pressure of a subject's eye even if the intraocular pressure is much higher than normal.

To achieve the object, the noncontact type tonometer according to one aspect of the present invention comprises a fluid discharging means for discharging fluid toward a cornea of the eye, a pressure detecting means for detecting discharge pressure of the fluid, a corneal transfiguration detecting means for detecting the transfiguration of the cornea, and a discharge stopping means for determining the precise moment for stopping the operation of the fluid discharging means according to the discharge pressure detected by the pressure detecting means.

The noncontact type tonometer according to another aspect of the present invention comprises a fluid discharging means for discharging fluid toward the cornea of the eye, a corneal transfiguration detecting means for detecting the transfiguration of the cornea, a timer for counting elapsed time, and a discharge stopping means for determining the precise moment for stopping the operation of the fluid discharging means according to the elapsed time counted by the timer.

According to the present invention, the stopping of the operation of the fluid discharging means can be changed according to the intraocular pressure of the eye and therefore measurement proper to the intraocular pressure can be carried out.

That is, according to the present invention, it is avoidable that the measurement of the intraocular pressure cannot be carried out when the intraocular pressure is high and, to the contrary, fluid is discharged by unnecessary high pressure when the intraocular pressure is low. In the two cases, the intraocular pressure measurement can be carried out such that the fluid is discharged by proper pressure corresponding to the intraocular pressure of the eye.

DETAILED DESCRIPTION OF THE PREFERRED EMBODIMENTS

Figure 1:
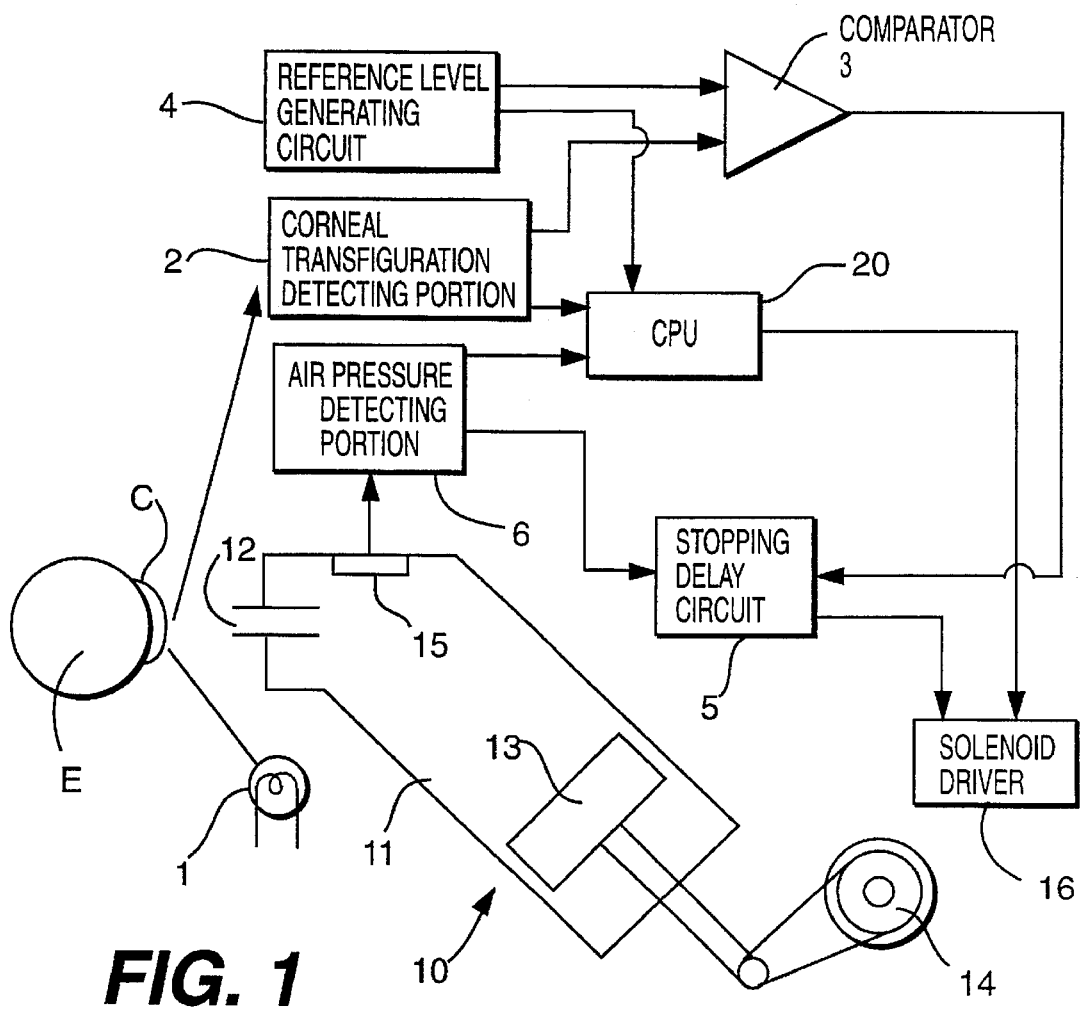
FIG. 1 is a block diagram showing a first embodiment of a noncontact type tonometer according to the present invention.

FIG. 1 is a block diagram showing a measuring portion and a gas discharging device of a noncontact type tonometer according to a first embodiment of the present invention.

The instrument in FIG. 1 comprises a light source 1 for illuminating a subject's eye E with detecting light, a corneal transfiguration detecting portion 2 for receiving reflected light from the eye E to detect a transfiguration state of a cornea C in terms of a change of light in quantity, and a fluid discharging device 10 for discharging fluid (air in this embodiment) toward the eye E to transfigure the cornea C of the eye E.

The fluid discharging device 10 comprises a cylinder 11, a nozzle 12 mounted in the cylinder 11 and facing the eye E, a piston 13 for pushing out air within the cylinder 11 from the nozzle 12, a rotary solenoid 14 as a driving means for driving the piston 13, and a pressure sensor 15 mounted in the cylinder 11 for measuring pressure therein.

A corneal transfiguration signal output by the corneal transfiguration detecting portion 2 is compared with a reference signal output by a reference level generating circuit 4 by means of a comparator 3 and is input into a central processing unit (hereinafter simply referred to as "CPU") 20. When the level of the corneal transfiguration signal coincides with that of the reference signal, the comparator 3 outputs a coincidence signal to a stopping delay circuit 5. The level of the reference signal is equal to that of the corneal transfiguration signal obtained when the cornea C is transfigured into a predetermined state before an applanation state (a flat state), in other words, the coincidence signal is output when the cornea C reaches the predetermined state before the applanation state.

On the other hand, a pressure detecting signal output by an air pressure detecting portion 6 which receives a signal from the pressure sensor 15 is input to the stopping delay circuit 5 and the CPU 20. The stopping delay circuit 5 functions as a fluid discharging stopping means for stopping discharging fluid. That is, the stopping delay circuit 5, based on a level P of a pressure detecting signal obtained when a coincidence signal from the comparator 3 is input thereinto, determines delay time T according to the formula T=P× constant (F) and outputs a stopping signal to a solenoid driver 16 when the delay time T elapses from a point of time when the coincidence signal is input.

The higher the intraocular pressure of the cornea C of the eye E, the higher the level of the pressure detecting signal obtained when the coincidence signal is generated. Further, since the discharge pressure increases with time, the length of the delay time corresponds to an increased quantity of the discharge pressure obtained after the coincidence signal is generated. Accordingly, by determining the delay time in proportion to the discharge pressure obtained when the coincidence signal is generated, the maximum of the discharge pressure can be made high when the intraocular pressure is high and can be made low when the intraocular pressure is low. That is, the proper maximum of the discharge pressure corresponding to the intraocular pressure can be determined.

After alignment of the instrument shown in FIG. 1 with respect to the eye E is completed or the CPU 20 receives a measurement starting signal from a measuring switch (not shown), the CPU 20 outputs a driving signal to the solenoid driver 16 to apply an electric current to the rotary solenoid 14, so that air within the cylinder 11 is compressed by the piston 13 and is discharged from the nozzle 12 toward the eye E.

Figure 2:
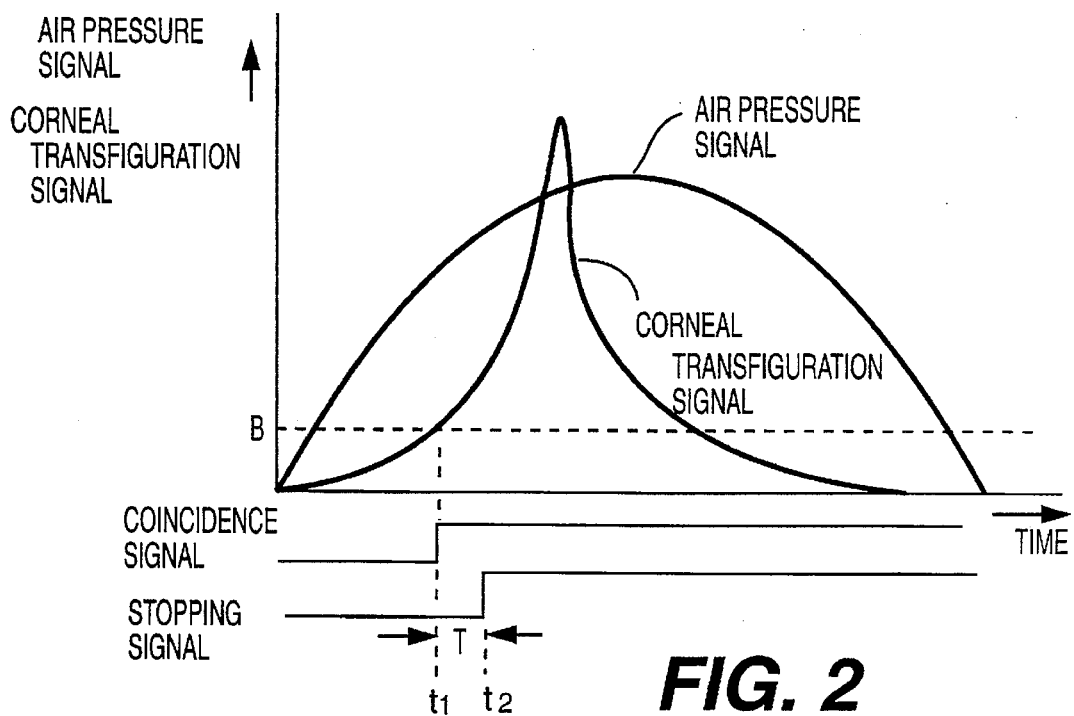
FIG. 2 is a graph showing a measurement result of the instrument shown in FIG. 1.

When the compressed air is discharged toward the eye E, the cornea C of the eye E is transfigured. As shown in FIG. 2, as the discharge pressure increases and the cornea approaches the applanation state, the corneal transfiguration signal output by the corneal transfiguration detecting portion 2 also gradually increases.

When the corneal transfiguration reaches the predetermined state before the applanation state and the corneal transfiguration signal exceeds a predetermined level B, the coincidence signal is output by the comparator 3 at the time point t1. The stopping delay circuit 5 determines the delay time T based on pressure P0 obtained when the coincidence signal is input and then the circuit 5 outputs a stopping signal to the solenoid driver 16 at the time point t2 at which the delay time T elapses. The solenoid driver 16 cuts the electric current sent to the rotary solenoid 14 when the stopping signal is input thereinto. Still, the discharge pressure continuously increases by inertia of the piston for a given period of time and then decreases.

Based on a pressure detecting signal P1 obtained when the corneal transfiguration signal reaches its peak, the CPU 20 calculates the intraocular pressure of the eye E by a predetermined conversion formula.

Figure 3A:
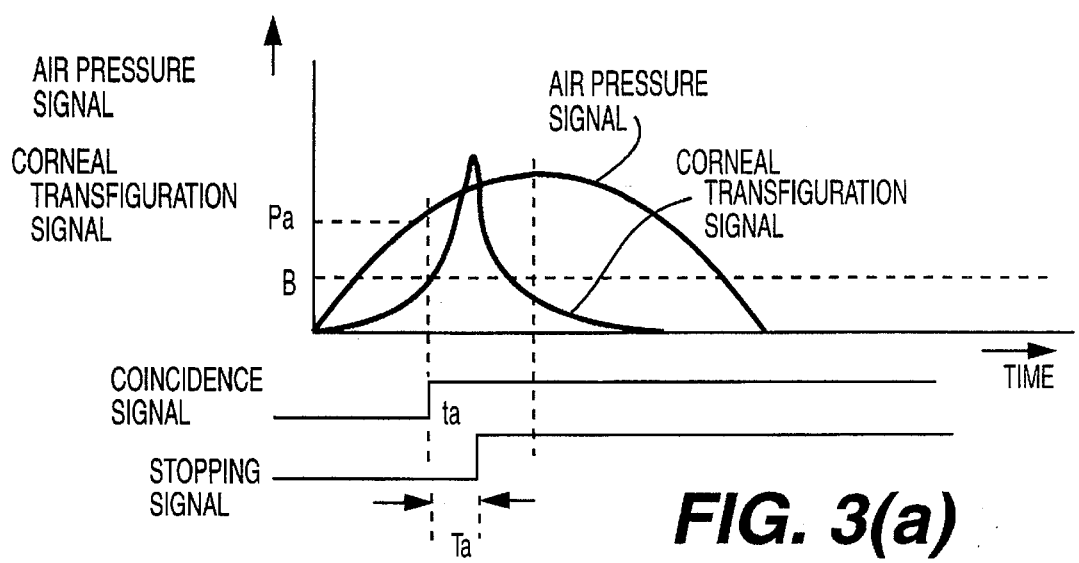
FIG. 3(a) is a graph showing a measurement result of the tonometer of the first embodiment obtained when intraocular pressure is low.
Figure 3B:
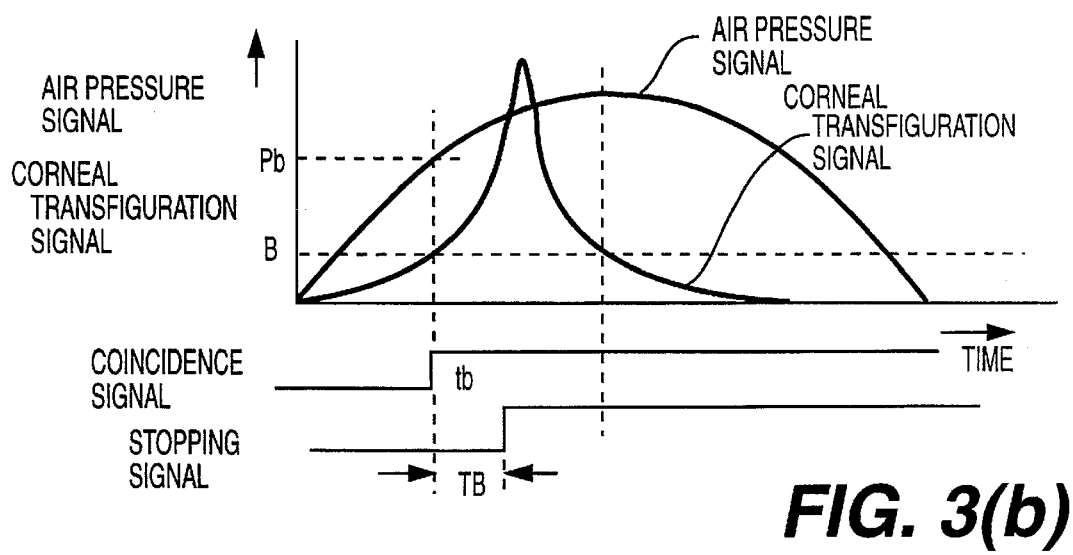
FIG. 3(b) is a graph showing a measurement result of the tonometer of the first embodiment obtained when intraocular pressure is normal.
Figure 3C:
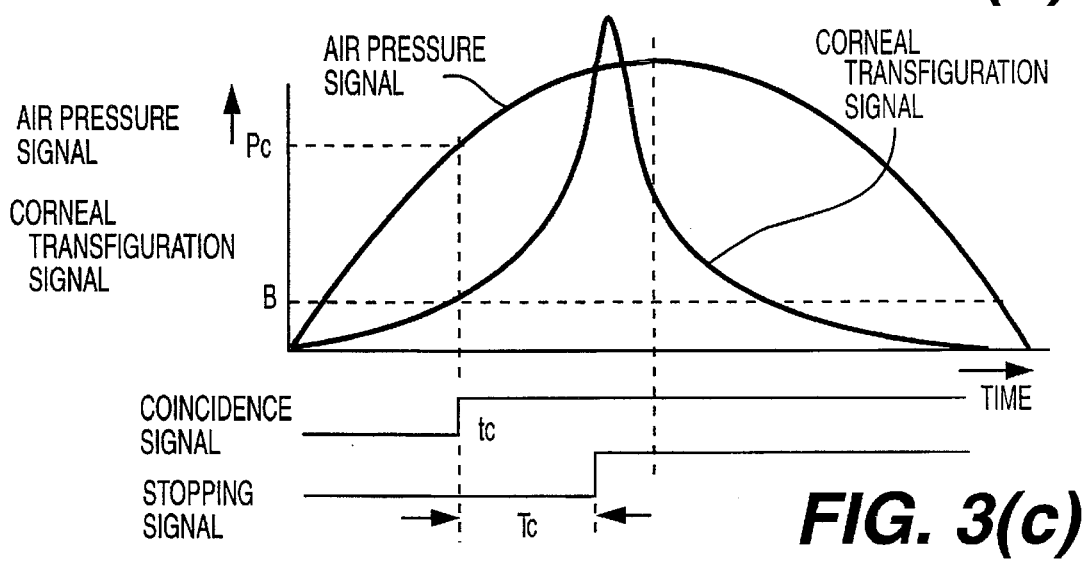
FIG. 3(c) is a graph showing a measurement result of the tonometer of the first embodiment obtained when intraocular pressure is high.

FIGS. 3(a) to 3(c) show examples of pressure signals and corneal transfiguration signals obtained when different intraocular pressures of the subject's eye are measured by the instrument of the above embodiment. FIG. 3(a) shows a case where the intraocular pressure is low, FIG. 3(b) shows a case where the intraocular pressure is normal, and FIG. 3(c) shows a case where the intraocular pressure is high.

The higher the intraocular pressure, the slower will be the change of the corneal transfiguration signal. Therefore the, time points ta, tb, tc at which a coincidence signal is each generated become gradually later, and in addition, respective values of pressure signals Pa, Pb, Pc corresponding to the time points become higher, and further, a period of time during which the cornea C is completely transfigured into an applanation state (a flat state) becomes longer. Accordingly, the delay time of each example, proportional to the values of the pressure signals Pa, Pb, Pc, is Ta<Tb<Tc.

Figure 4:
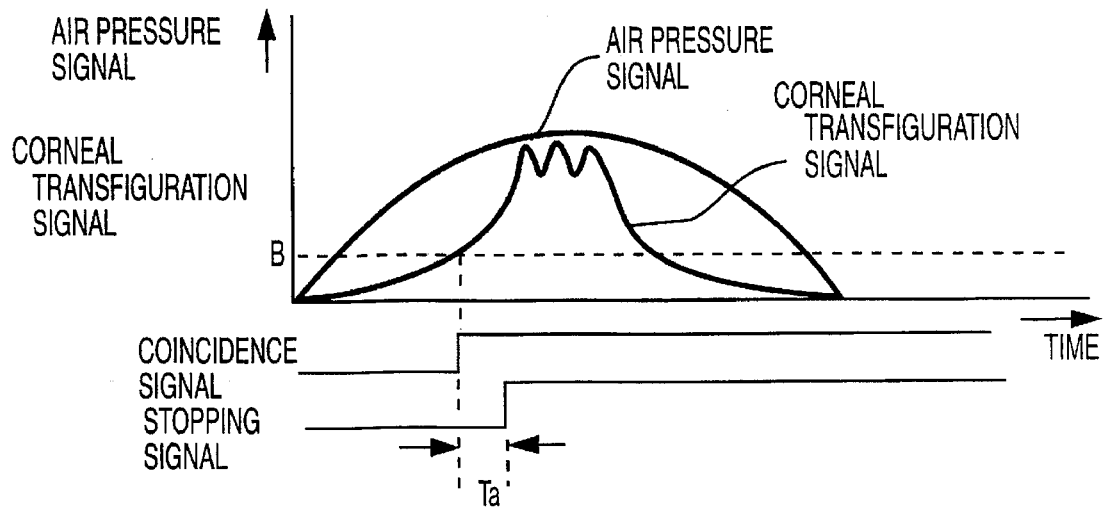
FIG. 4 is a graph showing a measurement result obtained when delay time Ta in FIG. 3(a) is applied to a subject's eye in FIG. 3(c).

FIG. 4 is a graph showing a case where the delay time Ta in FIG. 3(a) is applied, for comparison, to the eye E in FIG. 3(c). In this case, since the discharge pressure cannot rise to a high enough value to measure the intraocular pressure and decreases before the corneal transfiguration signal reaches its peak, the intraocular pressure measurement cannot be carried out.

Figure 5:
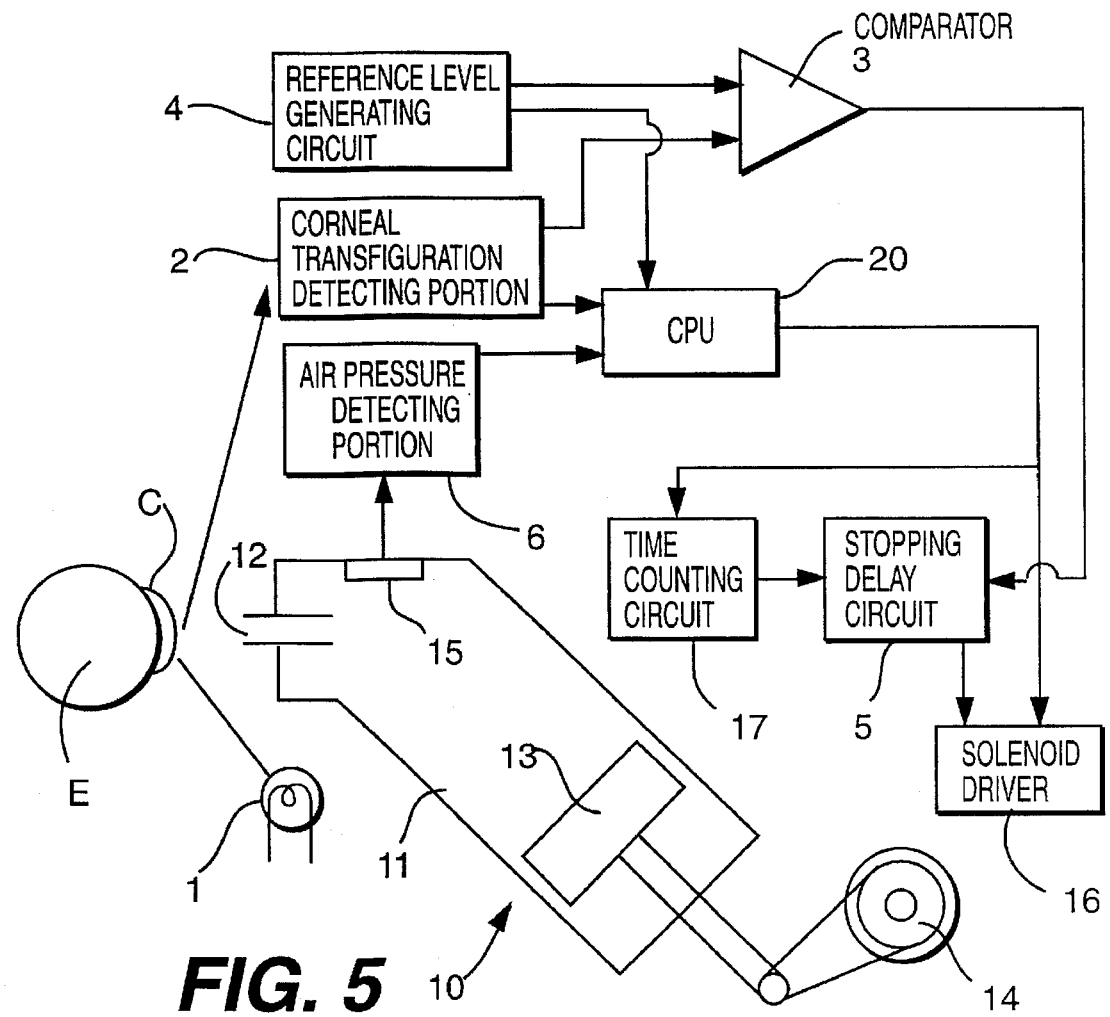
FIG. 5 is a block diagram showing a second embodiment of the noncontact type tonometer according to the present invention.

FIG. 5 is a block diagram showing a second embodiment of the noncontact type tonometer according to the present invention. The instrument shown in FIG. 5 includes the constitution shown in FIG. 1 and, in addition, includes a time counting circuit 17 for counting elapsed time after an electric current begins to be applied to the rotary solenoid 14. However, an output from the pressure detecting portion 6 is input to the CPU 20 only and is not input to the stopping delay circuit 5.

Figure 6:
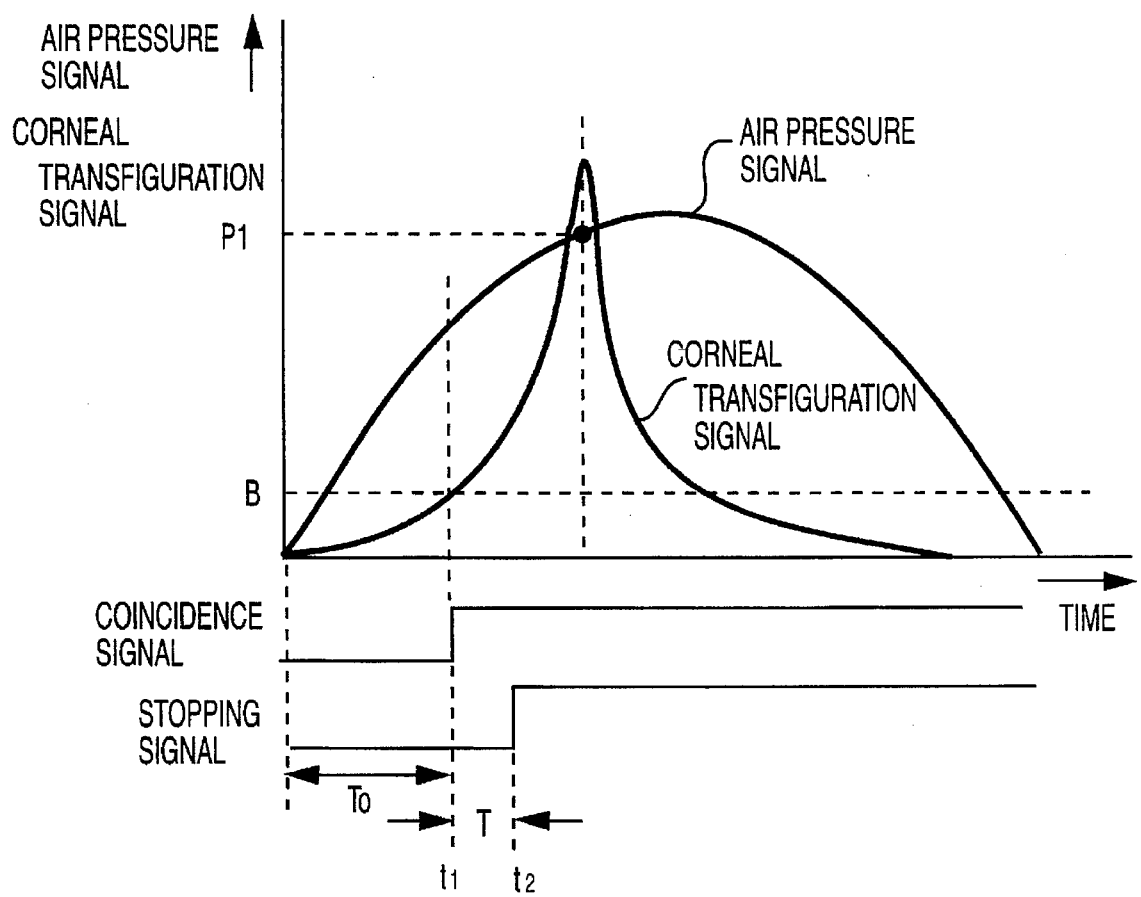
FIG. 6 is a graph showing a measurement result of the instrument shown in FIG. 5.

Since the elapsed time has a linear relationship to the rise in pressure, the intraocular pressure of the eye E also corresponds to the elapsed time. Based on the elapsed time, the instrument of the second embodiment determines delay time ranging from a point of time when the cornea C is transfigured into a predetermined state to a point of time when the fluid discharging device 10 is stopped. That is, as shown in FIG. 6, on the supposition that T0 is an elapsed time from the output of an coincidence signal, delay time T can be calculated by the formula T=T0×constant(F). The stopping delay circuit 5 outputs a stopping signal at the time point t2 at which the delay time T is over. The starting point of the delay time T is t1 at which an coincidence signal is output.

In the above embodiments, reference levels set in the reference level generating circuit 4 may be changed according to, for example, a first measurement result. Further, preferably, the constant(F) for calculating the delay time is changed. Further, these reference levels and constant(F) may be automatically changed by the CPU 20.

What is claimed is:

1. A noncontact type tonometer comprising:

means for discharging fluid toward a cornea of a subject's eye;

means for detecting discharge pressure of the fluid and for generating a discharge pressure signal;

means for detecting transfiguration of the cornea and for generating a corneal transfiguration signal;

means for generating a corneal transfiguration reference signal;

means for comparing the corneal transfiguration signal with the corneal transfiguration reference signal and for generating a coincidence signal before applanation of the cornea when the corneal transfiguration signal coincides with the corneal transfiguration reference signal;

means for generating a driving signal in response to the discharge pressure signal, the corneal transfiguration signal, and the corneal transfiguration reference signal;

means for determining when to stop operation of the means for discharging fluid after calculating a delay time according to the discharge pressure signal and the coincidence signal and for generating a stop signal; and means for controlling the means for discharging fluid according to the driving signal and the stop signal.

2. A noncontact type tonometer comprising:

means for discharging fluid toward a cornea of a subject's eye;

means for detecting discharge pressure of the fluid and for generating a fluid discharge pressure signal:

means for detecting transfiguration of the cornea and for generating a corneal transfiguration signal;

means for generating a corneal transfiguration reference signal;

means for comparing the corneal transfiguration signal with the corneal transfiguration reference signal and for generating a coincidence signal before applanation of the cornea when the corneal transfiguration signal coincides with the corneal transfiguration reference signal;

means for generating a driving signal in response to the discharge pressure signal, the corneal transfiguration signal, and the corneal transfiguration reference signal a timer for counting elapsed time of the driving signal and for generating a delay time signal;

means for determining when to stop operation of the means for discharging fluid according to the delay time signal and the coincidence signal and for generating a stop signal: and means for controlling the means for discharging fluid according to the driving signal and the stop signal.

* * * * *